United States Patent [19]

Pletcher

[11] Patent Number: 4,839,602

[45] Date of Patent: Jun. 13, 1989

[54] MEANS FOR DETECTING METAL IN A STREAM OF PARTICULATE MATTER

[75] Inventor: Charles D. Pletcher, Bon Air, Va.

[73] Assignee: Philip Morris Incorporated, New York, N.Y.

[21] Appl. No.: 927,276

[22] Filed: Nov. 4, 1986

[51] Int. Cl.[4] .......................................... G01R 27/16
[52] U.S. Cl. .............................. 324/57 Q; 324/71.4; 361/180
[58] Field of Search ............. 361/179, 180; 324/57 Q, 324/71.4, 59

[56] References Cited

U.S. PATENT DOCUMENTS

| | | | |
|---|---|---|---|
| 2,048,591 | 7/1936 | Berry | 175/182 |
| 2,550,607 | 4/1951 | Shoemaker | 175/183 |
| 2,580,670 | 1/1952 | Gilbert | 361/180 X |
| 2,587,631 | 3/1952 | Kuehne | 361/180 X |
| 2,709,785 | 5/1955 | Fielder | 324/71.4 X |
| 2,863,546 | 12/1958 | Josefowicz | 361/180 X |
| 3,030,576 | 4/1962 | Jaarsvelt et al. | 324/57 Q |
| 3,237,155 | 2/1966 | Brockett | 340/38 |
| 3,278,809 | 10/1966 | Brorein | 317/142 |
| 3,350,660 | 10/1967 | Endgahl et al. | 331/65 |
| 3,375,493 | 3/1968 | Gottlieb | 340/38 |
| 3,381,217 | 4/1968 | Williamson et al. | 324/41 |
| 3,457,465 | 7/1969 | Juranville | 317/146 |
| 3,460,000 | 8/1969 | Kiffmeyer | 317/148.5 |
| 3,721,859 | 3/1973 | Blanyer | 361/180 X |
| 3,727,075 | 4/1973 | Buckley et al. | 361/180 X |
| 3,747,010 | 7/1973 | Buck | 331/65 |
| 3,747,011 | 7/1973 | Buck | 331/65 |
| 3,747,012 | 7/1973 | Buck | 331/65 |
| 3,809,998 | 5/1974 | Mansson | 323/4 |
| 3,935,542 | 1/1976 | Buck | 331/65 |
| 3,961,238 | 6/1976 | Randolph, Jr. | 324/3 |
| 4,130,792 | 12/1978 | Sullivan | 324/3 |
| 4,138,709 | 2/1979 | Colwill | 361/180 |
| 4,193,023 | 3/1980 | Buck et al. | 323/19 |
| 4,220,499 | 9/1980 | Hughes, Jr. et al. | 324/71.4 X |
| 4,257,001 | 3/1981 | Partain et al. | 324/58.5 C |
| 4,291,280 | 9/1981 | Gardner | 331/65 |
| 4,553,040 | 11/1985 | Truper et al. | 307/116 |
| 4,613,830 | 9/1986 | Kamiya et al. | 331/65 |
| 4,663,542 | 5/1987 | Buck et al. | 361/180 X |

OTHER PUBLICATIONS

*The Encyclopedia of How It Works from Abacus to Zoom Lens,* (Clarke, D., ed.), "Metal Detectors" (A & W Publishers, Inc., New York, 1977), pp. 139–141.
*The Illustrated Science and Invention Encyclopedia,* (International Edition), "Metal Detectors" (H. S. Stuttman Inc., Westport, Conn., 1983), pp. 1488–1490.

*Primary Examiner*—A. D. Pellinen
*Assistant Examiner*—A. Jonathan Wysocki
*Attorney, Agent, or Firm*—Robert M. Isackson; Jeffrey H. Ingerman

[57] ABSTRACT

A device having a detector element for detecting small particles of metal moving in a stream of particulate matter, such as tobacco filler. The detector element is a coil through which the stream passes. The coil is the inductor of an oscillating circuit and is also part of the negative feedback loop of an operational amplifier. Inductance changes caused by the presence of metal become impedance changes that alter the amplifier gain, changing the amplitude of the AC component of an alternating current output signal. The signal peaks are shifted further, increasing detector amplitude, by coupling the signal through a capacitor to a source of potential so that the DC component of the signal also changes as the change in inductance allows current to flow through the capacitor.

18 Claims, 3 Drawing Sheets

MEANS FOR DETECTING METAL IN A STREAM OF PARTICULATE MATTER

BACKGROUND OF THE INVENTION

This invention relates to metal detectors. Particularly, this invention relates to metal detectors for detecting metallic objects in a stream of predominantly non-metallic particulate matter, such as a stream of tobacco filler in a cigarette rod.

Metallic objects may be present in tobacco filler from a number of sources—for example, wire used in the baling of tobacco, hardware (bolts, hinges, etc.) detached from the hogsheads in which the tobacco is stored and transported, and shavings and filings produced by the wearing of tobacco processing machinery. It is desirable to remove such foreign objects from the tobacco before it is incorporated into cigarettes.

As whole leaf tobacco is processed into cut filler, it is subjected to screening and sifting to remove foreign objects. Large magnets are typically used to remove ferromagnetic objects. However, some metallic objects still may remain in the tobacco filler which is delivered to cigarette making machines, particularly non-ferromagnetic objects, but also ferromagnetic particles.

Known metal detection apparatus is not suitable for detecting metal particles in a cigarette rod moving at hundreds or thousands of feet per minute on a high-speed cigarette maker. Any such particles are generally too small and move too quickly for detection by conventional metal detectors. Large particles may go undetected if they are not ferromagnetic. Although some large objects may puncture the cigarette wrapper and cause the cigarette containing the object to fail a pressure drop test and be rejected, some large objects may lie along the cigarette axis without puncturing the wrapper and not cause a rejection.

It would be desirable to be able to detect small metallic particles moving at high speed in a stream of particulate matter, such as in a cigarette rod.

It would also be desirable to be able to provide a metal detector that is sensitive to very small permeability changes introduced by small metallic particles passing through the detector and is not sensitive to changes in permeability occurring outside the detector, as may exist, for example, in cigarette manufacturing apparatus.

It would also be desirable to have a metal detector that can detect both non-ferromagnetic and ferromagnetic particles.

SUMMARY OF THE INVENTION

It is an object of this invention to be able to detect small metallic particles moving at high speed in a stream of particulate matter, such as in a cigarette rod.

It is another object to provide a metal detector that is sensitive to very small permeability changes introduced by small metallic particles passing through the detector and is not sensitive to changes in permeability occurring outside the detector, as may exist, for example, in cigarette manufacturing apparatus.

It is another object of this invention to provide a metal detector that can detect both non-ferromagnetic and ferromagnetic metallic particles.

In accordance with the present invention, there is provided apparatus for the detection of metal in a predominantly non-metallic sample. The apparatus comprises an oscillator circuit which provides an alternating current output signal and an analytical circuit which detects changes in the output signal, which changes indicate the presence of a metallic particle.

The oscillator circuit operates to provide an output signal having a characteristic frequency, AC amplitude, and DC baseline value when no metal is present in the sample (herein the "nominal condition"). The oscillator circuit includes a coil, preferably a multiturn inductor coil, having a passageway for passing the sample therethrough. The inductor coil forms an inductor element in the oscillator circuit and, in operation, generates a magnetic field interior to the coil in the passageway.

The permeability of a metallic particle passing through the passageway disturbs the steady state of the magnetic field and causes the inductance of the coil to change while the metal particle passes through the field. The change in inductance affects the oscillator circuit equilibrium and causes the output signal to change to an abnormal state while the particle is disturbing the field.

The output signal change is manifested in a shift in the AC amplitude and DC baseline of the output signal. The magnitude of the change is proportional to the permeability, size, and mass of the metal particle. For example, the permeability of gold may cause a decrease in amplitude and baseline, whereas the permeability of steel may cause an increase in amplitude and baseline, and the more metal present, the greater the shift may be.

The analytical circuit operates to detect the output signal, analyze it, and indicate when the output signal has changed from its nominal condition to an abnormal condition. The output signal is processed so that it can be compared to a signal corresponding to the nominal condition, whereby deviations from nominal condition, however brief, can be detected.

In the preferred embodiment, the analytical circuit determines the peak value and changes in the peak value, which can occur because of changes to the amplitude and baseline caused by the passage of metal through the inductor element.

The analytical circuit also may generate a marking signal that indicates the output signal is in an abnormal condition corresponding to the detection of one or more metal particles in the sample passing through the detector. The marking signal may be a visual or aural signal to alert an operator or a signal that can be input to an ejector device for removing the marked sample portion containing the metal particle or particles at an appropriate time and location.

BRIEF DESCRIPTION OF THE DRAWINGS

The above and other objects and advantages of the invention will be apparent on consideration of the following detailed description, taken in conjunction with the accompanying drawings, in which like reference characters refer to like parts throughout, and in which.

DETAILED DESCRIPTION OF THE INVENTION

The present invention, though it has other uses, is intended primarily for use on cigarette making machines to detect metallic objects in the cigarette rod produced by the machine. A preferred embodiment of the detector of the invention produces a signal which can be input to a rejection system, some type of which is found on most cigarette makers, which will cause the cigarette with which the signal is associated to be rejected.

As will be discussed more fully below, the sensing element of the detector of the present invention is an inductor element, preferably a multiturn cylindrical coil. A cylindrical multiturn coil is particularly suited for use on a cigarette machine. A cigarette machine is largely metallic, and therefore any detector must have a detection field of limited range. As is well known, the magnetic field density of a cylindrical multiturn coil is very high within the coil, and relatively low outside the coil. As the cigarette rod travels along the coil axis, it passes through the area of greatest magnetic field density where the pertubation of the magnetic field by the presence of a metallic particle, with the consequent change in inductance, has the greatest effect. The pertubation of the field outside the coil has little effect on the detector, thus minimizing interference from machinery, motors, moving metallic parts and magnetic fields exterior to the coil.

A round cigarette rod and a round coil work well together, maximizing the efficiency of the detector.

Other impedance elements whose impedance may vary from a nominal value when a metallic particle is brought proximate to the element may be used to alter the oscillator output signal.

Figure 1:
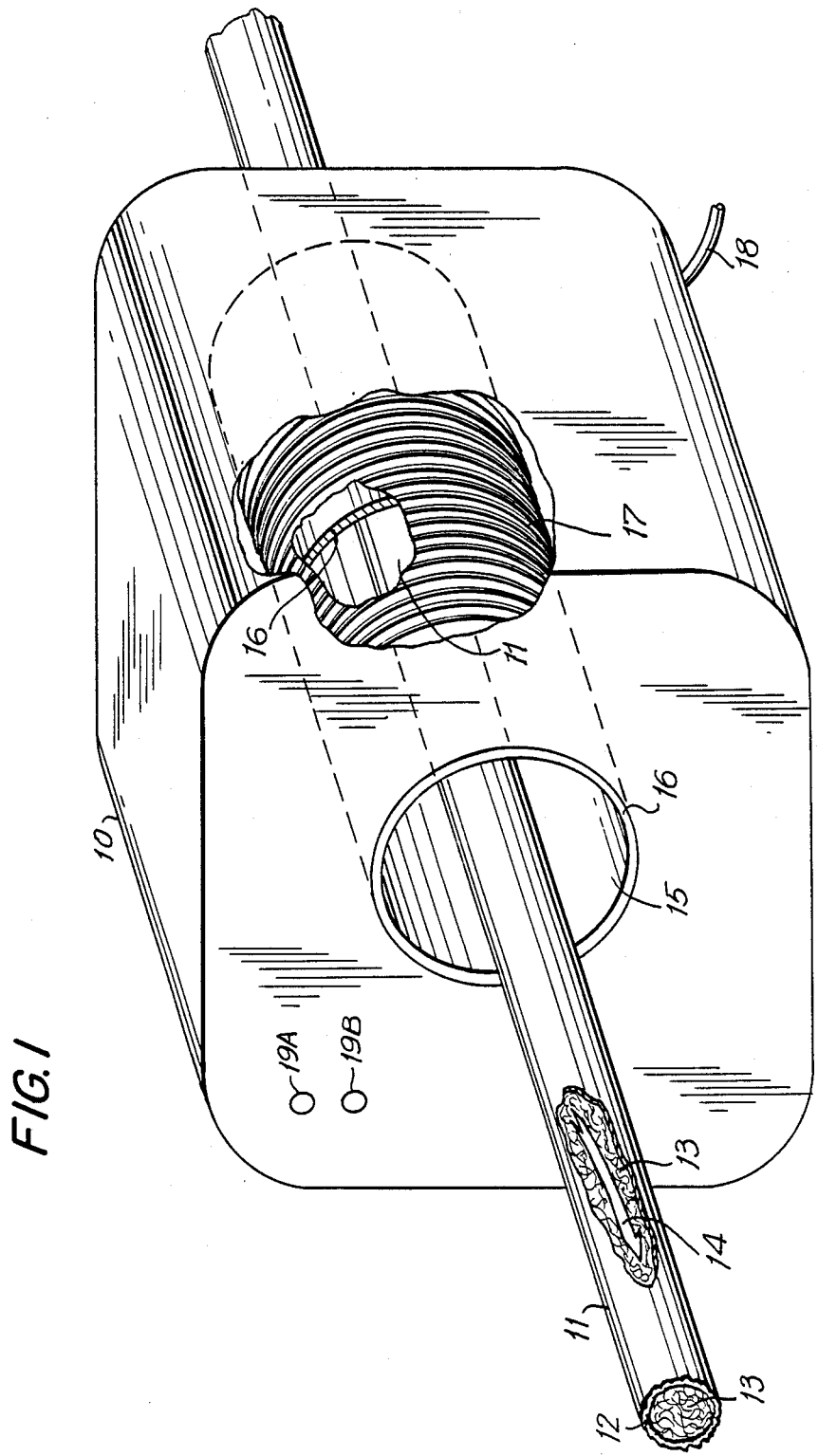
FIG. 1 is a partially fragmentary perspective view of a metal detector according to the present invention through which a cigarette rod is passing.

As seen in FIG. 1, detector 10 is mounted on a cigarette making machine (not shown) at a point beyond the formation point of cigarette rod 11 and preferably before rod 11 is cut into individual cigarettes. As can be seen, rod 11 has an outer layer of cigarette paper 12 wrapped around tobacco filler 13. An exemplary metal shaving is shown at 14.

Detector 10 includes a bore 15 through which rod 11 passes. In a preferred embodiment, bore 15 is a passtube made of a high-molecular-weight methacrylate plastic such as that sold under the trademark LEXAN®. A conductive wire is wound 40 times around passtube 16 to form a multiturn inductor coil 17 which is connected to the detector circuitry (not shown in FIG. 1). A cable 18 provides power to the detector circuitry and conducts the signals generated by the detector circuitry to, for example, the reject system (not shown) of the cigarette making machine. A light-emitting diode 19A is illuminated whenever detector 10 is operational. A second light-emitting diode 19B illuminates whenever metal is detected.

Figure 2:
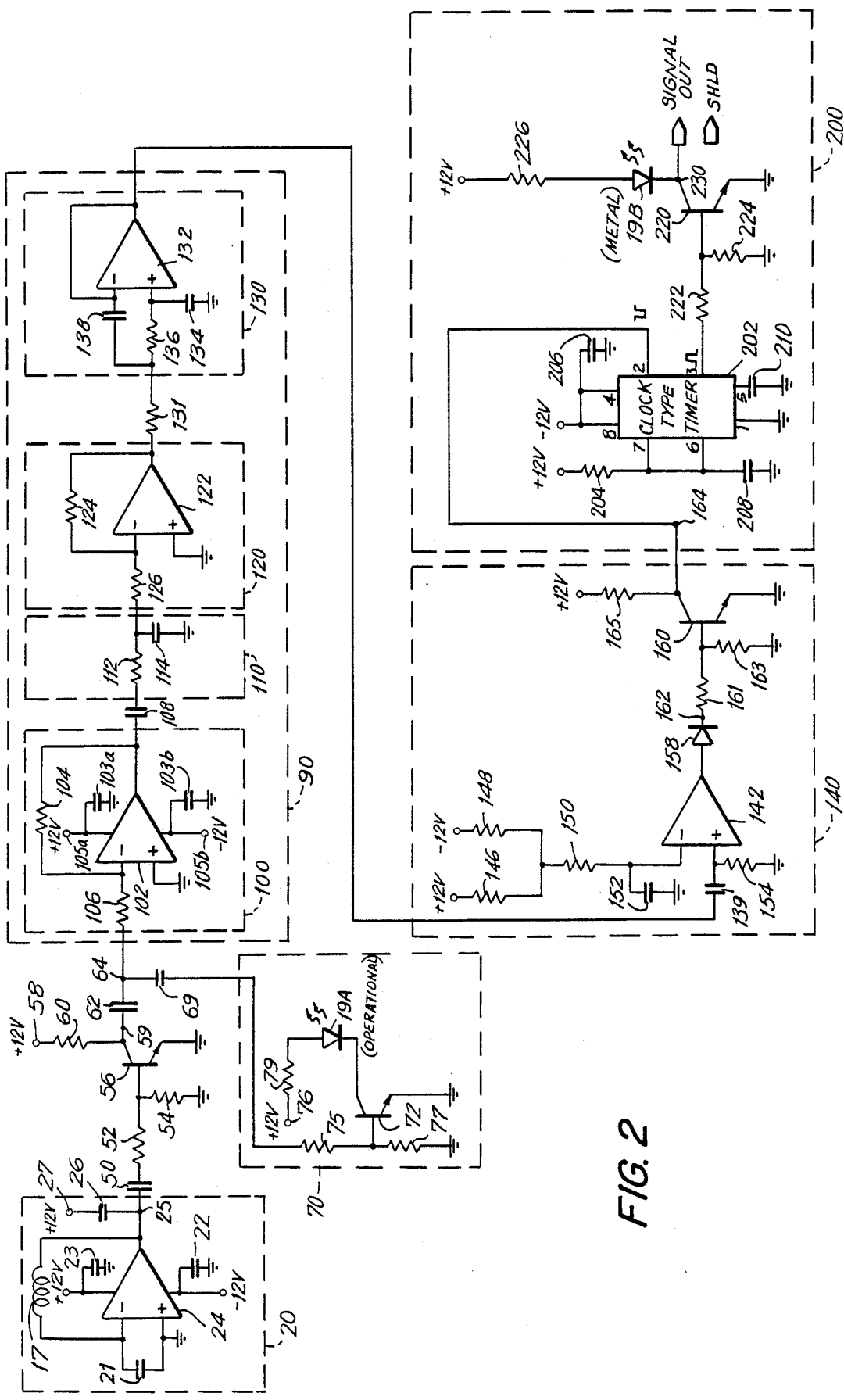
FIG. 2 is a schematic diagram of a circuit embodying the present invention.

A preferred embodiment of the detector circuitry is shown in FIG. 2. The oscillator circuit of detector 10 is shown in the dashed rectangle 20. Operational amplifier 24, inductor 17, and capacitors 21–23 are configured as shown to form an oscillator which preferably has a characteristic frequency in the range from 650 to 900 kHz, preferably about 760 kHz, under nominal conditions (i.e., no metal in the passtube 16). Inductor coil 17 of detector 10 is located in the negative feedback loop of operational amplifier 24 which is biased by capacitor 21 to produce an output signal oscillating about a baseline (DC component) of +5 volts under nominal conditions. Voltage source 27, typically +12 volts, fed across pull up capacitor 26 is added to the output of amplifier 24 at node 25.

Figure 3A:
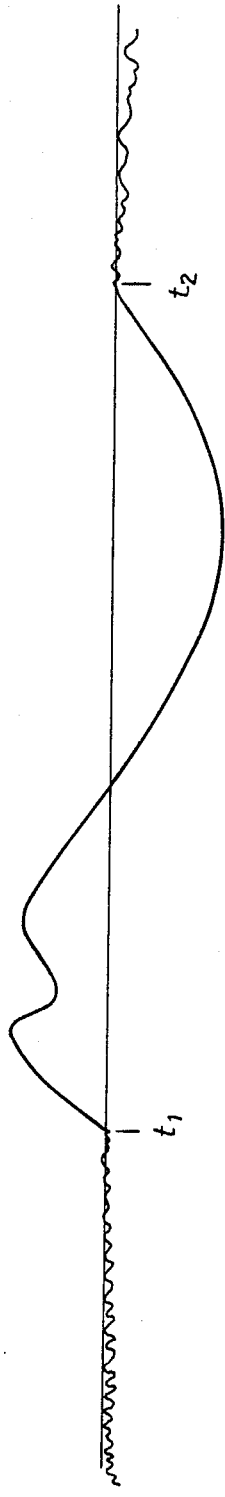
FIGS. 3 and 3A are graphic representations of the output signal of the oscillator circuit of FIG. 2 and a filtered output signal in the analytical circuit of FIG. 2, respectively.
Figure 3:
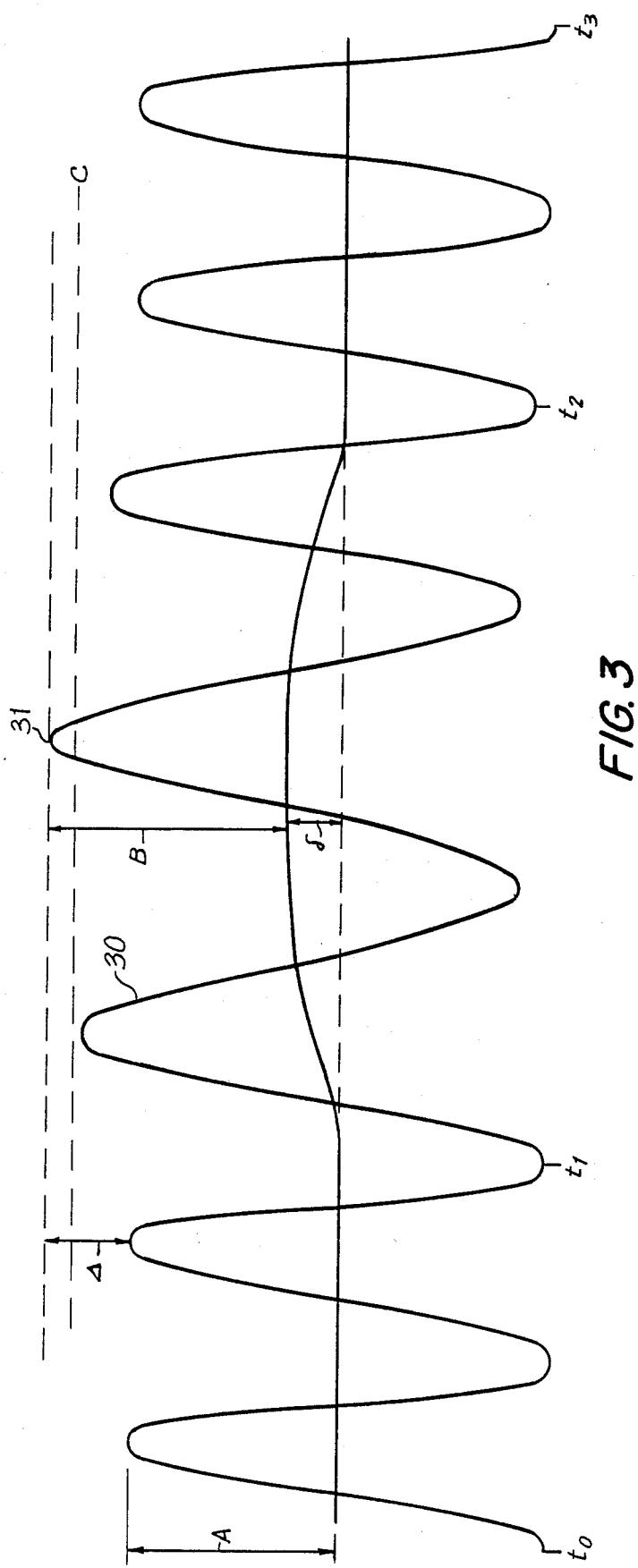

A representative output signal 30 produced at node 25 by circuit portion 20 is shown graphically in FIG. 3. Signal 30 ordinarily has amplitude A, typically about 6 volts, peak to peak, and a characteristic frequency of about 760 kHz. When a metallic object enters passtube 16, it changes the inductance of coil 17 by an amount that depends on its mass, size, and magnetic permeability. Such changes are independent of whether or not the metal is ferromagnetic.

The change of inductance of coil 17 has two effects of consequence in the present invention. First, it changes the impedance in the negative feedback loop of amplifier 24 which changes the gain of amplifier 24. Changing the gain changes the amplitude of the AC component of signal 30. Second, the change in inductance of coil 17 disturbs the steady state charge of capacitor 26, allowing signal current from voltage source 27 (+12 v) to flow through capacitor 26, coil 17 and capacitor 21 to ground. This changes the DC bias point of amplifier 24, thus altering the DC baseline component of signal 30. The change of inductance also causes a frequency change which plays no role in the present invention.

As shown by way of example in FIG. 3, the presence of an exemplary metallic particle passing through detector 10 causes the output signal 30 to change from the nominal condition, shown at time interval $t_0$–$t_1$, to an abnormal condition, shown at time interval $t_1$–$t_2$, and thereafter to return to the nominal condition, shown at time interval $t_2$–$t_3$. In changing from the nominal to abnormal condition, the amplitude of the AC component of signal 30 increases from A to B, and the DC baseline component increases by $\delta$, for a total absolute change of $\Delta$. If the detector apparatus, more specifically the analytical circuitry described below, is set to detect when output signal 30 is above or crosses a threshhold signal level represented by C, then the detector will indicate the presence of the exemplary metallic particle 14 causing such a change. For example, signal 30, as depicted in time interval $t_1$–$t_2$ would result in the detection of a metal object. However, if oscillator circuit 20 did not alter the DC baseline component as well as the AC component, the peak 31 of signal 30 would not exceed C for the same exemplary metallic particle 14. Thus the circuit shown in FIG. 2 increases detector sensitivity by shifting both the DC baseline component and the amplitude of the AC component.

The analytical circuitry shown in FIG. 2 comprises filter circuit 90 for filtering and analyzing signal 30 and providing a filtered signal corresponding to the baseline and amplitude of the output signal including both nominal and abnormal conditions, comparative circuit 140 for comparing the filtered signal to a threshold signal and providing an output signal representing the detection of a metal particle when the filtered signal is greater than the threshold value, and a metal-detected indicator 200 which indicates that a metallic particle has been detected, e.g., by illuminating light emitting diode 19B, providing a reject trigger signal, or both. The analytical circuitry typically also includes indicator circuit 70 for indicating when the device is operational, e.g., by illuminating light emitting diode 19A.

The detection of a metal particle causes a baseline and amplitude shift in signal 30. In the preferred embodiment, the DC baseline and AC amplitude shift combine to modulate onto the characteristic frequency a lower frequency signal, typically with a positive-going pulse and a negative-going pulse in tandem, the pulses being of about equal magnitude. Any frequency shift to the characteristic frequency caused by the metal particle can be ignored because any shift is small and frequencies near and above the characteristic frequency are filtered out as explained below. By substantially suppressing the characteristic frequency, the pulses corresponding to the DC baseline and AC amplitude shift remain and, after amplification, can be readily detected.

Incorporating the DC baseline shift to the change provides greater sensitivity, permitting detection of extremely small non-ferromagnetic and ferromagnetic particles. The DC baseline shift may be momentary, and may be restored to the nominal baseline by capacitor 26, which begins charging shortly after it discharges, depending on its time constant. Moreover, AC coupling capacitors are used to minimize any DC baseline shift injected by power fluctuation, amplification, or other equipment interference. Because the analytical circuit looks at the onset of the change, even a momentary shift in DC baseline will be detected in addition to the AC amplitude change, and any subsequent suppression of the DC baseline shift by a coupling capacitor does not affect detection of metallic particles.

In the preferred embodiment, signal 30 is AC coupled by capacitor 50 and passed across resistors 52 and 54 to the base of buffer transistor 56. Voltage source 58, typically a +12 volt source, is fed through resistor 60 to the collector of transistor 56, and the emitter of transistor 56 is grounded. Signal 30 thus turns on transistor 56 and the signal generated at node 59 is AC coupled by capacitor 62 to provide a basically sinusoidal output signal 30 at node 64. This signal is then AC coupled by capacitor 69 to an optional indicator circuit 70 which comprises driver transistor 72, light emitting diode (LED) 19A, voltage source 76 (+12V), and resistors 75, 77 and 79 configured as shown. Transistor 72 is biased on when no signal is input to the base of transistor 72. When signal 30 is passed to the base of transistor 72, the AC waveform causes LED 19A to turn on and off alternately at the frequency of signal 30. Because this cycling of LED 19A is faster than the eye can detect, it appears to be on continuously. Thus, LED 19A indicates that the detector is operating.

Signal 30 at node 64 is also fed to filter circuit 90 which comprises high gain amplifier 100, passive low pass filter 110, amplifier 120, and active low pass filter 130. Amplifier 100 provides high gain inverted amplification of signal 30 in order to be able to detect the small changes in DC baseline and AC amplitude riding on the characteristic frequency after amplified signal 30 is low pass filtered. Amplifier 100 includes operational amplifier 102, which has control voltage sources 105a at ±12 volts and 105b at −12 volts fed across respective grounded capacitors 103a and 103b to suppress noise, a grounded non-inverting input, resistor 104 in the feedback loop, and input resistor 106 to the inverting input. The values of resistors are selected to provide a high gain, for example, about 47.

Amplified signal 30 is then AC coupled by capacitor 108 to passive low pass filter 110 including resistor 112 and capacitor 114 having values selected to pass only frequencies below the characteristic frequency. Filter 100 is tuned to reject (or pass to ground) as much of the characteristic frequency and higher frequencies as possible, including any frequency shift caused by the presence of a metal particle, while minimizing rejection of the lower frequency signal pulse components of output signal 30 caused by the metal particle.

The bandwidth of the lower frequency signals may vary depending upon the size of the particle. The longer the permeability is changed, the more it affects the bandwidth, up to a point. Signals for larger particles have been found from 18 kHz as compared to just below 750 kHz for extremely small particles. Pulse width times as large as 1.0 millisecond have been found. It is believed that the charge stored in capacitor 114 may aid in increasing the pulse width due to a temporary discharge at the onset of an abnormal output signal 30 increasing the duration of the abnormal condition.

With the characteristic frequency suppressed, the change impressed upon the nominal signal 30 becomes more significant. The filtered signal output from filter 110 is then amplified by amplifier 120 which consists of operational amplifier 122 having a grounded non-inverting input, feedback resistor 124, and inverting input resistor 126. The values of resistors 124 and 126 may be selected to provide a gain of about 54.

The amplified signal 30 output from amplifier 120 is coupled by input resistor 131 to active low pass filter 130 tuned to suppress the characteristic frequency (and higher frequencies) and noise. Filter 130 is configured as shown and includes operational amplifier 132, and filtered and amplified signal 30 is input both to the non-inverting input through resistor 136 and across grounded capacitor 134, and to the inverting input by capacitor 138.

The output of filter 130 is then AC coupled by capacitor 139 to comparator circuit 140. Comparator 140 includes operational amplifier 142 having at its inverting input a bias or threshhold signal which is provided by a +12 volt source across resistor 146 in parallel with a −12 volt source across resistor 148, which signals are added and passed through a low pass filter including resistor 150 and capacitor 152 to filter out noise. The values of resistors 146 and 148 may be adjusted to set the comparator at the selected bias or threshold voltage level. The AC coupled output of filter 130 is passed across grounded resistor 154 to the non-inverting input. The output of amplifier 142 is connected to diode 158 which is forward biased to pass the positive output signal to the base of buffer transistor 160 across resistors 161 and 163 configured as shown. A +12 volt source is passed across resistor 165 to the collector of transistor 160.

When no metal is present, the bias voltage causes amplifier 142 to have a negative output which open-circuits diode 158 and turns buffer transistor 160 off. When a metallic particle is present it causes a shift in the DC baseline and AC amplitude of signal 30. After the higher frequencies are filtered out by filter 90, the remaining pulse components, shown in FIG. 3A, are input to comparator 142. When the voltage value of the pulse components rises above the bias or threshold voltage, comparator 142 provides a positive output which closes diode 158 and turns on buffer transistor 160. When the filtered and amplified signal falls below the bias voltage, comparator 142 turns off, which opens diode 158 and turns off buffer transistor 160. Thus, comparator 142 puts out a positive square pulse signal at node 162 and transistor 160 provides a respective negative square pulse signal at node 164, both pulses corresponding to the detected metal particle.

The signal from node 164 is input to metal-detected indicator circuit 200 which comprises a single shot output circuit based on a 555 clock type timer 202 having a 5.2 msec pulse width. Timer 202 is configured as shown with a +12 volt source, resistor 204, and capacitors 206, 208, and 210 to provide a positive pulse upon the detection of the falling edge of the signal from node 164.

The positive pulse output of timer 202 is input to the base of driver transistor 220 across resistors 222 and 224. The driver transistor emitter is grounded and the collector is biased by a +12 volt source fed through resistor 226 in series with light emitting diode 19B which is oriented so that when timer 202 output is at the nominal condition, driver transistor 220 is off, and LED 19B is biased open and off. When a pulse is output from timer 202, it turns on transistor 220 which closes LED 19B which in turn emits light for the length of the pulse width. The pulse also causes the signal at node 230 to go from the bias voltage level, corresponding to a logical high state of e.g., +12 volts, to a short-circuited voltage level when transistor 220 is turned on, corresponding to logical low state, e.g., +0 volts, for the duration of the pulse. The signal at node 230 can be used as a reject signal to input to a control circuit, typically a logic control circuit, for rejecting the sample containing the metal particle at an appropriate time and location. For example, cigarettes corresponding to the detected pulse as identified by the trigger signal can be rejected after the pressure drop test, whether or not the cigarette passes the pressure drop test.

The ±12 volts power supplies may be from any conventional regulated source. In the preferred embodiment, the detector utilizes the power supply from the cigarette manufacturing machine and uses two conventional voltage regulators internal to the detector unit to provide better signal stability and reduce any noise component that might be present in the power supply of the machine or its related circuitry. Lowering the noise level enhances the sensitivity of the apparatus.

The increased sensitivity of the metal detector of the present invention allows the detection of particles as small as 1.0 mm, which are precisely the kinds of particles not detected by previous metal detectors. Moreover, it also readily detects both ferromagnetic and non-ferromagnetic particles. The detector also works best at the high speeds characteristic of cigarette making machines e.g., 1,033 feet per minute, because of the dynamic action of the oscillating circuit. In fact, larger pieces of metal inserted very slowly into a detector of the present invention may not be detected because, at low speeds, any inductance change caused by the entry of the metal object, and the change in capacitance affecting the DC bias, may be integrated out over the time constant of the oscillator circuit. With appropriate redesign and adjustment of time constants, however, detectors of the present invention may be adapted for use with slower moving samples.

Thus a metal detector is provided which can be used to detect small particles moving at speeds such as those found in a cigarette maker. One skilled in the art will appreciate that the present invention can be practiced by other than the described embodiments, which are presented for purposes of illustration and not of limitation, and the present invention is limited only by the claims which follow.

What is claimed is:

1. Apparatus for detecting metal in a sample, said apparatus comprising:
    an oscillator circuit, said circuit producing an output signal having a characteristic frequency and having, under nominal conditions, a characteristic AC amplitude and oscillating, under nominal conditions, about a characteristic DC baseline, said circuit including an impedance element having a nominal impedance;
    means for passing a sample through the impedance element so that the impedance of the impedance element changes in response to the presence of metal in the sample which in turn changes the DC baseline value and AC amplitude of the output signal; and
    analytical circuit means for determining when the output signal changes from its nominal DC baseline and AC amplitude.

2. The apparatus of claim 1 wherein the impedance element further comprises an inductor element and the nominal impedance is a nominal inductance.

3. The apparatus of claim 2 wherein the oscillator circuit means further comprises an AC amplifier means and the inductor element is coupled in series between the inverting input and the output of the amplifier means whereby metal passing through the inductor element causes a change in the inductance of the inductor element and the gain of the amplifier, thereby causing the output signal amplitude to vary from the characteristic amplitude.

4. The apparatus of claim 3 wherein said oscillator circuit further comprises a voltage source coupled by a capacitor to the output of the amplifier means whereby the change in inductance of the inductor element thereby varies the DC baseline value of the output signal.

5. The apparatus of claim 2 wherein said analytical circuit means further comprises comparator mean for comparing absolute peak values of said output signal to a predetermined threshold.

6. The apparatus of claim 5 wherein the analytical circuit means further comprises:
    filter means for substantially removing the characteristic frequency from the output signal; and
    amplifier means for amplifying the signal; wherein:
    said comparator means compares the amplified and filtered signal to a threshold signal so that when the amplified and filtered signal is greater than the threshold signal, said comparator means produces a signal corresponding to detection of a metal particle.

7. Apparatus for detecting metal in a sample, said apparatus comprising:
    an oscillator circuit, said circuit producing an output signal having a characteristic frequency and having, under nominal conditions, a characteristic AC amplitude, said alternating current signal oscillating, under nominal conditions, about a characteristic DC baseline said circuit including an induction element having a nominal inductance;
    means for passing a sample through the inductor element so that the inductance of the inductor element changes in response to the presence of metal in the sample which in turn changes the DC baseline value and AC amplitude of the output signal; and analytical circuit means for determining when the output signal changes from its nominal baseline and amplitude; said oscillator circuit further including:

amplifier means, the inductor element being coupled in series between the inverting input and the output of the amplifier means whereby metal passing through the inductor element causes a change in the inductance of the inductor element and the gain of the amplifier, thereby causing the output signal AC amplitude to vary from the characteristic AC amplitude; and a voltage source coupled by a capacitor to the output of the amplifier means whereby the change in inductance of the inductor element thereby varies the DC baseline value of the output signal.

8. The apparatus of claim 7 wherein said analytical circuit means is for detecting absolute changes in peak value of said output signal caused by changes in said AC amplitude from said characteristic AC amplitude and changes in said DC baseline from said characteristic DC baseline.

9. The apparatus of claim 8 wherein said analytical circuit means comprises comparator means for comparing absolute peak values of said output signal to a predetermined threshold.

10. The apparatus of claim 9 wherein the analytical circuit means further comprises:

filter means for substantially removing the characteristic frequency from the output signal; and amplifier means for amplifying the filtered signal; wherein:

said comparator means compares the amplified filtered signal to a threshold signal so that when the amplified filtered signal is greater than the threshold signal, said comparator means produces a signal corresponding to detection of a metal particle.

11. Apparatus for detection of metal in a stream of particulate matter, said apparatus comprising:

an oscillator circuit, said circuit producing an output signal having a characteristic frequency and having, under nominal conditions, a characteristic AC amplitude, said output signal oscillating, under nominal conditions, about a characteristic DC baseline said circuit including an indulation element having a nominal inductance;

means for passing a stream of particulate matter through the inductor element so that the inductance of the inductor element changes in response to the presence of metal in the stream of particulate matter which in turn changes the DC baseline value and AC amplitude of the output signal; and analytical circuit means for determining when the output signal changes from its nominal DC baseline and AC amplitude; said oscillator circuit further including:

amplifier means, the inductor element being coupled in series between the inverting input and the output of the amplifier means whereby metal passing through the inductor element causes a change in the inductance of the inductor element and the gain of the amplifier, thereby causing the output signal AC amplitude to vary from the characteristic AC amplitude; and a voltage source coupled by a capacitor to the output of the amplifier means whereby the change in inductance of the inductor element thereby varies the DC baseline value of the output signal.

12. The apparatus of claim 11 wherein said analytical circuit means is for detecting absolute changes in peak value of said output signal caused by changes in said AC amplitude from said characteristic AC amplitude and changes in said DC baseline from said characteristic baseline.

13. The apparatus of claim 12 wherein said analytical circuit means comprises comparator mean for comparing absolute peak values of said output signal to a predetermined threshold.

14. The apparatus of claim 13 wherein the analytical circuit means further comprises:

low pass filter means for substantially removing the characteristic and higher frequencies from the output signal; and amplifier means for amplifying the filtered signal components; wherein:

said comparator means compares the amplified filtered signal to a threshold signal so that when the amplified filtered signal is greater than the threshold signal, said comparator means produces a signal corresponding to detection of a metal particle.

15. Apparatus for detection of metal in a cigarette rod, said apparatus comprising:

an oscillator circuit, said circuit producing an output signal having a characteristic frequency and having, under nominal conditions, a characteristic AC amplitude, said output signal oscillating, under nominal conditions, about a characteristic DC baseline said circuit including our induction element having a nominal inductance;

means for passing a cigarette rod through the inductor element so that the inductance of the inductor element changes in response to the presence of metal in the cigarette rod which in turn changes the DC baseline value and AC amplitude of the output signal; and analytical circuit means for determining when the output signal changes from its nominal DC baseline and AC amplitude; said oscillating circuit further including:

amplifier means, the inductor element being coupled in series between the inverting input and the output of the amplifier means whereby metal passing through the inductor element causes a change in the inductance of the inductor element and the gain of the amplifier, thereby causing the output signal AC amplitude to vary from the characteristic AC amplitude; and a voltage source coupled by a capacitor to the output of the amplifier means whereby the change in inductance of the inductor element thereby varies the DC gaseline value of the output signal.

16. The apparatus of claim 15 wherein said analytical circuit means is for detecting absolute changes in peak value of said output signal caused by changes in said AC amplitude from said characteristic AC amplitude and changes in said DC baseline from said characteristic DC baseline.

17. The apparatus of claim 16 wherein said analytical circuit means comprises comparator means for comparing absolute peak values of said output signal to a predetermined threshold.

18. The apparatus of claim 17 wherein the analytical circuit means further comprises:

low pass filter means for substantially removing the characteristic and higher frequencies from the output signal; and amplifier means for amplifying the remaining signal components; wherein:

said comparator means compares the amplified remaining signal components signal to a threshold signal so that when the amplified remaining signal is greater than the threshold signal, said comparator means produces a signal corresponding to detection of a metal particle.

* * * * *

UNITED STATES PATENT AND TRADEMARK OFFICE
CERTIFICATE OF CORRECTION

PATENT NO.  : 4,839,602
DATED       : June 13, 1989
INVENTOR(S) : Charles D. Pletcher It is certified that error appears in the above-identified patent and that said Letters Patent is hereby corrected as shown below:

Column 8, line 24, delete "AC"

Column 8, line 31, before "amplitude" insert --AC--

Column 10, line 6, before "baseline" (second occurence) insert --DC--

Column 10, line 30, "our induction" should be --an inductor--

Column 10, line 53 "gaseline" should be --baseline--

Signed and Sealed this

Twenty-first Day of August, 1990

Attest:

HARRY F. MANBECK, JR.

Attesting Officer

Commissioner of Patents and Trademarks